(12) United States Patent
Naef et al.

(10) Patent No.: US 7,112,699 B2
(45) Date of Patent: Sep. 26, 2006

(54) PROCESS FOR THE DIRECT CONVERSION OF LACTONES INTO UNSATURATED KETONES OR ALDEHYDES

(75) Inventors: Ferdinand Naef, Carouge (CH); Wolfgang Giersch, Bernex (CH)

(73) Assignee: Firmenich SA, Geneva (CH)

( * ) Notice: Subject to any disclaimer, the term of this patent is extended or adjusted under 35 U.S.C. 154(b) by 73 days.

(21) Appl. No.: 11/228,603

(22) Filed: Sep. 16, 2005

(65) Prior Publication Data

US 2006/0036116 A1    Feb. 16, 2006

Related U.S. Application Data

(63) Continuation of application No. PCT/IB2004/001153, filed on Apr. 1, 2004.

(30) Foreign Application Priority Data

Apr. 10, 2003    (WO) .................. PCT/IB03/01426

(51) Int. Cl.
*C07C 45/41* (2006.01)
(52) U.S. Cl. .............. 568/346; 568/397; 568/446; 568/484
(58) Field of Classification Search ............. None
See application file for complete search history.

(56) References Cited

U.S. PATENT DOCUMENTS 2,053,845 A   9/1936 Schmidt et al. .......... 260/138
2,612,524 A   9/1952 Zettlemoyer et al. ..... 260/590
2,739,158 A * 3/1956 Caldwell ................. 549/329
4,950,799 A   8/1990 Hargis .................... 568/484

FOREIGN PATENT DOCUMENTS

EP    0 539 274 B1    4/1996

OTHER PUBLICATIONS

Snider et al. A New Route to Funtionalized trans-Hydrindenones. Journal of the American Chemical Society, 1983, vol. 105, p. 2364-2368.*
Johnston et al. Samarium(II)-Mediated 4-exo trig Ketyl-Olefin Cyclisation of Unsaturated Aldehydes. A General, Stereoselective Synthesis of Functionalised Cyclobutanols.☐☐Tetrahedron Letters, 1999, vol. 40, p. 4913-4916.*
Kim et al. Ate Complex from Diisobutylaluminum Hydride and n-Butyllithium as a Powerful and Selective Reducing Agent fro the Reduction of Selected Organic Compounds Containing Various Fucntion Groups. Journal of Organic Chemistry, 1984, 49, p. 1717-1724.*
Barry B. Snider et al., "A New Route To Functionalized *trans*-Hydrindenones", Journal. American Chemical Society, vol. 105, No. 8, pp. 2364-2368 (1983).

* cited by examiner

*Primary Examiner*—Sikarl A. Witherspoon
(74) *Attorney, Agent, or Firm*—Winston & Strawn LLP

(57) ABSTRACT

The present invention refers to a process for the preparation of unsaturated ketones or aldehydes by pyrolysis of a lactone, in the presence of a reducing agent such as molecular hydrogen or a carboxylic acid, and in the presence of a catalyst, optionally supported, comprising at least one metal selected from the group consisting of Y, Ti, Cd, Mn, Zn, Sc and Zr.

11 Claims, No Drawings

PROCESS FOR THE DIRECT CONVERSION OF LACTONES INTO UNSATURATED KETONES OR ALDEHYDES

CROSS-REFERENCE TO RELATED APPLICATIONS

This application is a continuation of International application PCT/IB2004/001153 filed 1$^{st}$ Apr. 2004, the entire content of which is expressly incorporated herein by reference thereto.

TECHNICAL FIELD

The present invention relates to the field of organic synthesis. More particularly, it refers to the reduction of a lactone into the corresponding unsaturated aldehyde by the means of a Piria type reaction, using particular catalysts.

BACKGROUND

The reductive pyrolysis of a carboxylic acid or ester, i.e. of a substrate wherein the carboxylic functional group is not part of a ring, into the corresponding aldehyde or ketone is a quite known type of reaction. For example, one may cite the processes described in U.S. Pat. No. 2,053,845 or more recently in U.S. Pat. No. 4,950,799.

In contrast, to the best of our knowledge, the reductive pyrolysis of a substrate wherein the carboxylic functional group is part of a ring has been reported only once, in EP 539274, wherein a cyclic anhydride is reduced into the corresponding di-aldehyde.

In fact the general formulae of the substrates described in the prior art, and in particular in EP 539274, exclude the use of lactones as reactant. The prior art does not teach, nor suggest, a process for the reductive pyrolysis of a lactone, and even less the reduction, into the corresponding unsaturated aldehyde or ketone, i.e. a reaction wherein in a single step there is reduced a carboxylic function and a carbon-carbon double bond is formed in a specific position.

SUMMARY OF THE INVENTION

The invention related a process for the preparation of unsaturated ketones or aldehydes by pyrolysis of a lactone in the presence of a reducing agent and of a catalyst comprising at least one metal selected from the group consisting of Y, Ti, Cd, Mn, Zn, Sc and Zr.

DETAILED DESCRIPTION OF THE PREFERRED EMBODIMENTS

We have now surprisingly discovered that it is possible to pyrolyse a lactone to produce an unsaturated carbonyl derivative. Indeed, the present invention relates to a process for the pyrolytic reduction of a lactone, having at least one hydrogen atom vicinal to the endocyclic oxygen atom of the lactone functional group, into the corresponding unsaturated ketone or aldehyde; said process being performed in the presence of a reducing agent selected from the group consisting of carboxylic acids having a boiling point below 300° C. and molecular hydrogen, and of a catalyst, optionally supported, comprising at least one metal selected from the group consisting of Y, Ti, Cd, Mn, Zn, Sc and Zr.

By "corresponding unsaturated ketone or aldehyde" we mean here a ketone or aldehyde which could be obtained by formally transforming the lactone into the corresponding hydroxy-acid, converting said hydroxy-acid into the corresponding hydroxy-ketone or aldehyde and then dehydrating the latter, as exemplified in the formal process of Scheme 1:

Scheme 1:

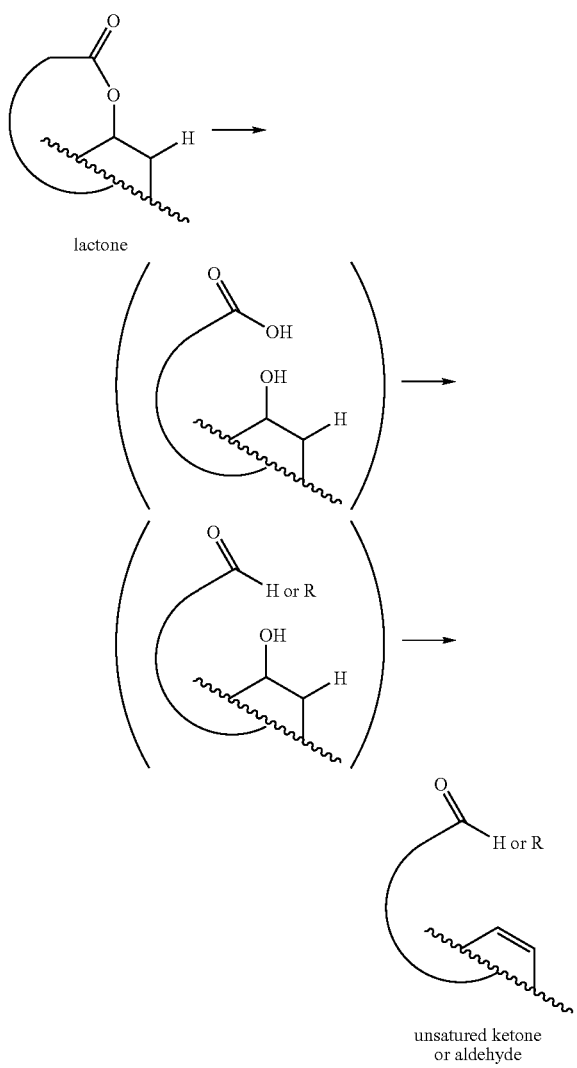

wherein the brackets mean that the species is hypothetical.

By "lactone having at least one hydrogen atom vicinal to the endocyclic oxygen atom of the lactone functional group" we mean here a lactone having at least one hydrogen atom on a carbon atom marked by an asterisk in the general structure of scheme 2:

Scheme 2:

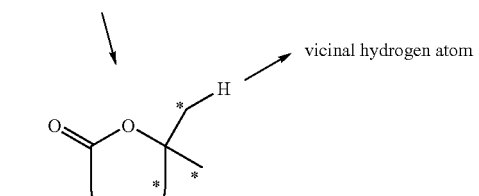

* = carbon atom which may carry a hydrogen atom vicinal to the endocyclic oxygen The invention's pyrolysis is preferably performed in the vapor phase. Generally speaking, a vapor stream, comprising the gaseous lactone, or substrate, and the gaseous reducing agent, is contacted with, or passed through, a useful catalyst.

As a consequence of such experimental condition a useful substrate should have significant vapor pressure at the temperature and pressure of the process. By "significant vapor pressure" we mean here a vapor pressure of at least 0.2 bar at 300° C.

Moreover, it is desirable that said substrate, prior to its contact with the catalyst, does not degrade or decompose spontaneously once heated at the process' temperature.

According to an embodiment of the invention, the invention's process concerns the pyrolytic reduction of a lactone of formula

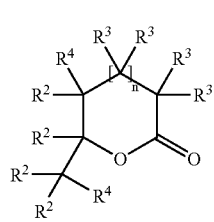
(I)

wherein n represents an integer from 0 to 3;

the $R^2$ groups represent each a hydrogen atom or a linear, branched or cyclic $C_1$ to $C_8$ alkyl, alkenyl, alkadienyl group; at least two of said $R^2$ groups may be bonded together to form a mono- or bi-cyclic $C_5$ to $C_{12}$ saturated or unsaturated rings, said ring being optionally substituted by one or two $C_{1-4}$ alkyl groups;

one or two $R^3$ groups represent each a $R^2$ group and the other $R^3$ groups represent each a hydrogen atom; and one of the $R^4$ groups represents a hydrogen atom and the other $R^4$ group represents a $R^2$ group;

into the corresponding unsaturated ketone or aldehyde of formula (II) or (III), or a mixture thereof,

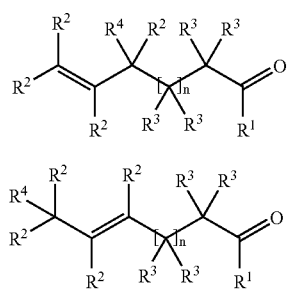

wherein n, $R^2$, $R^3$ and $R^4$ are as defined in formula (I), the $R^1$ group represents a hydrogen atom or a $C_1$ to $C_{10}$ alkyl group, and the carbon-carbon double bond has a configuration of the type (Z) or (E) or a mixture of the two configurations. In particular, $R^1$ may represent a hydrogen atom or a methyl, ethyl, n-propyl or n-butyl group, or even more preferably a hydrogen atom or a methyl or ethyl group.

As should be evident from formula (I), by "saturated or unsaturated rings" it is meant here a ring that is not aromatic.

It is also understood that the exact nature of the product obtained by the invention's process will depend, amongst other factors, on the chemical structure of the starting lactone (I). Indeed, depending on the exact nature of each $R^4$ group, i.e. if only one or both of them are hydrogen atoms, one may obtain only a product of formula (I), or (II), or alternatively a mixture thereof.

According to a further embodiment of the invention, the invention's process concerns the pyrolytic reduction of a lactone of formula

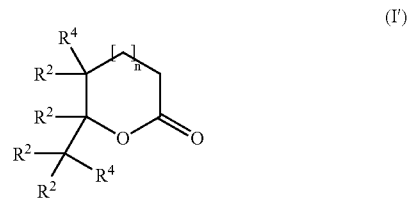
(I')

wherein n represents 0 or 1, preferably 0;

the $R^2$ groups represent each a hydrogen atom or a linear, branched or cyclic $C_3$ to $C_8$ alkyl or alkenyl group; two of said $R^2$ groups may be bonded together to form a mono- or bi-cyiclic $C_5$ to $C_{12}$ saturated or unsaturated ring, said ring being possibly substituted by one or two $C_{1-4}$ alkyl groups;

one of the $R^4$ groups represents a hydrogen atom and the other $R^4$ group represents a $R^2$ group, preferably both $R^4$ are a hydrogen atom;

into the corresponding unsaturated ketone or aldehyde of formula (II') or (III'), or a mixture thereof,

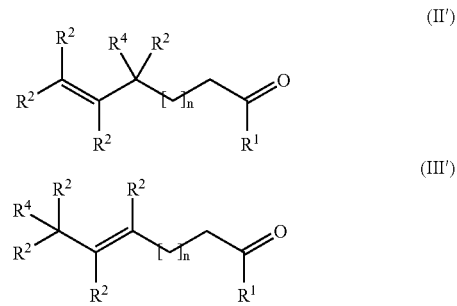

wherein n, $R^2$, $R^3$ and $R^4$ are as defined as hereinabove, the carbon-carbon double bond has a configuration of the type (Z) or (E) or a mixture of the two configurations, and $R^1$ represents a hydrogen atom or a methyl, ethyl, n-propyl or n-butyl group, preferably a hydrogen atom or a methyl or ethyl group.

According to a more particular embodiment of the invention, a suitable substrate is of formula (IV) or (V)

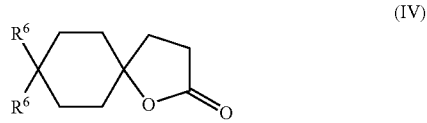
(IV)

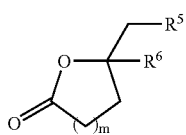
(V)

wherein m represents 1 or 2, $R^5$ represents a hydrogen atom or a linear or branched $C_1$ to $C_6$ alkyl or alkenyl radical and $R^6$ represents a hydrogen atom or a $C_{1-4}$ alkyl group.

The invention's process requires the presence of a catalyst comprising at least one metal selected from the group consisting of Y, Ti, Cd, Mn, Zn, Sc and Zr.

According to a particular embodiment of the invention said catalyst comprises at least one metal selected from the group consisting of Mn, Zn, Sc and Zr.

An example of mixed catalyst, i.e. comprising more than one metal, is represented by a mixture of Mn and Zn compounds, wherein preferably the Mn/Zn molar ratio is comprised between 0.7 and 1.3, or even approximately 1.

The catalyst can be used as such, i.e. in a powdered or granular form, or in a supported form.

According to an other embodiment of the invention, the catalysts is preferably used in a supported form, i.e. deposited on an organic or inorganic support which is chemically stable under the reaction conditions. In such a case, according to an embodiment of the invention, the total amount of metals represents between 2 and 20% w/w of the supported catalyst.

Suitable supports comprise fine or coarse pumice, aluminium oxide, silica, silicagel or activated charcoal. By "fine or coarse" we mean here particles having a mean diameter below 0.3 cm in the case of fine ones, and between 0.3 and 1.5 cm in the case of coarse ones.

According to a particular embodiment of the invention, catalysts supported on fine pumice have proved to be particularly attractive.

Specific, but not limiting, examples of suitable catalysts include oxides or hydroxides of at least one of the metals cited above.

Other suitable examples are the supported catalysts obtainable by a reaction comprising the following step:

i) absorb or adsorb, on a support, a solution of a soluble salt of one or more of the metals cited above, in neutral or acidic water, to obtain a pre-catalyst;
ii) optionally wash said pre-catalyst with an aqueous base, such as an alkaline carbonate, bicarbonate or hydroxyde;
iii) dry and pyrolize the pre-catalyst, under air, at a temperature comprised between 300° C. and 500° C. to obtain the supported catalyst, and
iv) optionally reduce, at least partially, the supported catalyst with a $C_1$–$C_3$ alcohol, such as methanol, under an inert gas, such as nitrogen, and at a temperature comprised between 300° C. and 500° C.

Specific, but not limiting, examples of soluble salts are Mn(II), Zn(II), Sc(III) or Zr(IV) sulfates, acetates, nitrates and halide.

A specific example of preparation will be described further below.

A suitable reducing agent is a compound selected from the group consisting of carboxylic acids having a boiling point below 300° C. and molecular hydrogen. In particular the reducing agent can be chosen amongst molecular hydrogen ($H_2$), formic acid and the carboxylic acids of formula $R^1COOH$, $R^1$ representing a $C_1$ to $C_{10}$ radical.

The nature of the reducing agent used determines the nature of the final product, i.e. an aldehyde or a ketone. Indeed, the use of ($H_2$) or formic acid provides an aldehyde, while the use of a carboxylic acid having at least two carbon atoms provides a ketone.

According to a suitable embodiment of the invention, the reducing agent is molecular hydrogen, formic acid or acetic, propionic, butanoic or pentanoic acid. More preferably, the reducing agent is molecular hydrogen or formic, acetic or propionic acid.

The reducing agent is advantageously used in at least a stoechiometric amount in respect of the substrate. However, it is understood that said agent could also be used in large excess, with respect to the substrate, in order to maximize the yield of the final product. For example, in the case it is used molecular hydrogen or formic acid, the substrate/reducing agent molar ratio can be comprised between 1/5 and 1/20, while in the case it is used a $R^1COOH$ acid, said ratio can be comprised between 1/1 and 1/3.

It is interesting to point out that, surprisingly, when $H_2$ is used, the reduction of the carbon-carbon double bond of the final product is not observed, although said product is contacted with hot $H_2$ in the presence of a reduction catalyst.

It is also interesting to point out that, surprisingly, the carbon-carbon double bond formed is not isomerised to form for example an enone derivative, at least in significant amounts, despite the presence of metals and high temperatures.

As mentioned above the invention's process is carried out in the vapor phase. Therefore, the temperature and the pressure can play an important role. Indeed both temperature and pressure must be chosen in order to enable the maintenance of the substrate and of the reducing agent, and preferably also of the product of the reaction, in the vapor phase during their contact with the catalyst. Moreover, the temperature must be sufficiently high to promote the reaction itself.

Having said that, it has to be mentioned that the process's temperature and pressure depend also on the exact nature of the substrate and of the reducing agent. Therefore, generally speaking, it is not possible to provide precise temperature and pressure values; however a skilled person in the art will be perfectly able to select said values by performing a very limited number of routine experiments.

In any case, according to a particular embodiment of the invention, we have found that suitable temperatures are comprised between 300° C. and 500° C., preferably between 380° C. and 420° C. Similarly, suitable pressures are comprised between 0.5 bar and 1.5 bar; preferably the process is performed at approximately ambient pressure.

According to a particular embodiment, a practical way to carry out the invention's process is to generate, using any known tool, a vapor mixture comprising the substrate, the reducing agent and optionally an inert solvent, and then inject said vapor mixture over, or through, the catalyst with a suitable flow. The vapor mixture, prior its contact with the catalyst, may also be diluted by an inert gas, such as nitrogen, argon or helium.

More precisely, in this procedure, a preformed solution of the reducing agent and substrate, optionally in an inert solvent, is contacted slowly with the heated catalyst and is transformed into a vapor mixture. The vapor mixture thus generated is then pushed through the catalyst by means of a nitrogen flow, at a suitable speed. Specific examples of inert solvent are tetrahydrofurane (THF) or toluene.

The speed at which the vapor mixture is passed over the catalyst should be sufficiently low in order to allow the reaction to occur. It is not possible to provide precise speed values or flows, as said values will depend on the chosen temperature, pressure and substrate, as well as on the dimension of the column containing the catalyst. However, we have found that a flow allowing a contact time of the vapors with the catalyst which is comprised between 10 and 60 seconds can be used advantageously.

EXAMPLES

The invention will now be described in further detail by way of the following example, wherein the abbreviations have the usual meaning in the art, the temperatures are indicated in degrees centigrade (° C.) and all the abbreviations have the usual meaning in the art.

Example

Experimental Procedure for the Pyrolysis of Various Lactones

Preparation of the Catalyst and of the Apparatus

Procedure a)

To a solution of 140 g of MnSO4·$H_2O$ in 200 ml of water were added 200 g of pumice granule (average diameter: 0.5–1.5 cm). After 1 hour of stirring, the pumice was filtered and washed several times with a saturated $Na_2CO_3$ water solution and finally with distilled water. The pumice thus obtained was dried at 400° C. and, still at the same temperature, 100 ml of MeOH were added slowly over the pumice.

A quartz column (diameter: 2.8 cm, length: 150 cm) was packed with 100 g of the pumice obtained above. The column, at the exception of the two extremities, was inserted into an oven. One of the two extremities was connected with a gas inlet and a syringe inlet, while the second one was connected with two traps, one cooled at 0–1° C. and the second at −78° C.

Procedure b)

To a solution of 2.5 g of $Zn(OAc)_2·2H_2O$ and 2.5 g of $Mn(OAc)_2$ in 100 ml of water were added 50 g of pumice granule (average diameter: 0.5–1.5 cm). After 1 hour of stirring at 50° C. the mixture was kept overnight at room temperature. Then, after concentration (rotary evaporator), the mixture was dried in a column at 430° C. during 12 hours.

Procedure c)

To a solution of $Zr(OAc)_4$ (15% in acetic acid) in 30 ml of water were added 30 g of pumice granule (average diameter: 0.5–1.5 cm). After staying 24 hours at room temperature, the mixture was concentrated and dried in a column at 500° C. overnight.

Pyrolysis

Procedure A)

A solution consisting of 8-tert-butyl-1-oxaspiro[4.5]decan-2-one (obtained according to the literature) (2.7 g, 12.9 mmoles) into 6.8 g of HCOOH was added dropwise, via a syringe, over the supported catalyst (obtained according to procedure a) at 450° C. and with a $N_2$ steam (ca. 10 ml/minute). A few minutes after the end of the addition, the products coming out of the column, and collected by the two traps, were combined and diluted into EtOEt. The organic layer thus obtained, after having been washed twice with 10 ml of water, was evaporated on a rotary evaporator. The residue was distilled (bulb to bulb, 0.2 mbar, oven=190°) to recover 1.5 g of a 2/1 mixture of 3-(4-tert-butyl-1-cyclohexen-1and of the starting lactone (conversion: 50%; yield of aldehyde: 66%).

Procedure B)

Using the same procedure as described under A) but starting with a solution consisting of 1-oxa-spiro[4.11]hexadecan-2-one (obtained according to the literature) (3.1 g, 22.5 mmoles) into 27 g of HCOOH and a supported catalyst obtained according to procedure b), there were obtained 1.8 g of the corresponding 3-(1-cyclodocecen-1-yl)propanal (purity: 48%; yield: 31,5%).

MS (final compound): 222 (24); 178 (75); 163 (20); 149 (33); 135 (59); 121 (43), 109 (75); 95 (87); 81 (98); 67 (100); 55 (92); 41 (88).

Procedure C)

Using the same procedure as described under A) but starting with a solution consisting of γ-nonalactone (obtained according to the literature) (5.0 g, 32.0 mmoles) into 45 g of acetic acid and a supported catalyst obtained according to procedure a), there were obtained (after bulb to bulb distillation at 40 mbar, oven=190°) 3.6 g of the corresponding 5-decen-2-one (purity: 70%; yield: 52%).

MS (final compound): 154 (3); 125 (3); 111 (5); 96 (18); 81 (22); 67 (13); 54 (22); 43 (100).

Procedure D)

Using the same procedure as described under A) but starting with a solution consisting of δ-nonalactone (obtained according to the literature) (3.1 g, 22.5 mmoles) into 27 g of HCOOH and a supported catalyst obtained according to procedure b), there were obtained (after bulb to bulb distillation at 0.14 mbar, oven=110°) 1.38 g of the corresponding 5-nonenal (purity: 30%; yield: 15.3%).

MS (final compound): 140 (2); 122 (14); 95 (42); 84 (100); 67 (51); 55 (78); 41 (86).

Procedure E)

Using the same procedure as described under A) but starting with a solution consisting of 1-oxa-spiro [4.5]decan-2-one (obtained according to the literature) (3.0 g, 19.5 mmoles) into 27 g of HCOOH and a supported catalyst obtained according to procedure c), there were obtained (after bulb to bulb distillation at 9 mbar, oven=110°) 2.6 g of a mixture of the 3-(1-cyclohexen-1-yl)propanal (51%) and of the starting lactone (22%).

MS (final compound): 138 (9); 120 (11); 109 (13); 94 (88); 79 (100); 67 (42); 55 (16); 41 (27).

Procedure F)

Using the same procedure as described under A) but starting with a solution consisting of octahydrocoumarine (22 g, 145 mmoles) into 58 g of acetic acid and a supported catalyst obtained according to procedure a), there were obtained (after bulb to bulb distillation at 42 mbar, oven=175°) 10.4 g of 4-(1-cyclohexen-1-yl)-2-butanone (purity: 71%; yield: 33%).

MS (final compound): 152 (37); 109 (52); 94 (100); 79 (88); 67 (49); 43 (38).

What is claimed is:

1. A process for the pyrolytic reduction of a lactone, having at least one hydrogen atom vicinal to the endocyclic oxygen atom of the lactone functional group, into an unsaturated ketone or aldehyde; said process being performed in the presence of:
 a reducing agent selected from the group consisting of carboxylic acids having a boiling point below 300° C. and molecular hydrogen; and
 a catalyst, optionally supported, comprising at least one metal selected from the group consisting of Y, Ti, Cd, Mn, Zn, Sc and Zr.

2. A process according to claim 1, wherein the pyrolysis is performed in the vapor phase and said lactone has a vapor pressure of at least 0.2 bar at 300° C.

3. A process according to claim 1, wherein the lactone is of formula

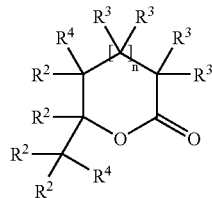
(I)

wherein n represents an integer from 0 to 3;
 the $R^2$ groups represent each a hydrogen atom or a linear, branched or cyclic $C_1$ to $C_8$ alkyl, alkenyl, alkadienyl group; at least two of said $R^2$ groups may be bonded together to form a mono- or bi-cyclic $C_5$ to $C_{12}$ saturated or unsaturated rings, said ring being optionally substituted by one or two $C_{1-4}$ alkyl groups;
 one or two $R^3$ groups represent each a $R^2$ group and the other $R^3$ groups represent each a hydrogen atom; and
 one of the $R^4$ groups represents a hydrogen atom and the other $R^4$ group represents a $R^2$ group;
 into the corresponding unsaturated ketone or aldehyde of formula (II) or (III), or a mixture thereof,

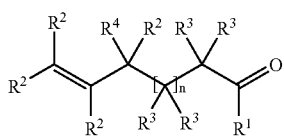
(II)

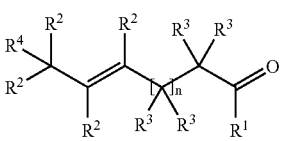
(III)

wherein n, $R^2$, $R^3$ and $R^4$ are as defined in formula (I), the $R^1$ group represents a hydrogen atom or a $C_1$ to $C_{10}$ alkyl group, and the carbon-carbon double bond has a configuration of the type (Z) or (E) or a mixture of the two configurations.

4. A process according to claim 1, wherein the lactone is of formula (IV) or (V)

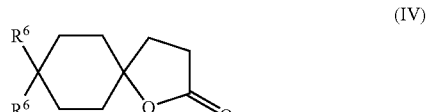
(IV)

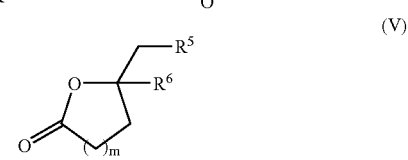
(V)

wherein m represents 1 or 2, $R^5$ represents a hydrogen atom or linear or branched $C_1$ to $C_6$ alkyl or alkenyl radical and $R^6$ represents a hydrogen atom or a $C_{1-4}$ alkyl group.

5. A process according to claim 1, wherein the catalyst comprises at least one metal selected from the group consisting of Mn, Zn, Sc and Zr.

6. A process according to claim 1, wherein the catalyst is deposited on a organic or inorganic support.

7. A process according to claim 1, wherein the support is selected from the group consisting of fine and course pumice, aluminium oxide, silica, silicagel and activated charcoal.

8. A process according to claim 1, wherein the catalyst is selected from oxides or hydroxides of at least one of the metals.

9. A process according to claim 1, wherein the catalyst is obtainable by a reaction comprising the following step:
 i) absorb or adsorb, on a support, a solution of a soluble salt of one or more of the metals cited above, in neutral or acidic water, to obtain a pre-catalyst;
 ii) optionally wash said pre-catalyst with an aqueous base, such as an alkaline carbonate, bicarbonate or hydroxyde;
 iii) dry and pyrolize the pre-catalyst, under air, at a temperature comprised between 300° C. and 500° C. to obtain the supported catalyst, and
 iv) optionally reduce, at least partially, the supported catalyst with a $C_1$–$C_3$ alcohol, such as methanol, under an inert gas, such as nitrogen, and at a temperature comprised between 300° C. and 500° C.

10. A process according to claim 1, wherein the reducing agent is selected from the group consisting of molecular hydrogen, formic acid, and a carboxylic acid of formula $R^1COOH$, $R^1$ representing a $C_1$ to $C_{10}$ radical.

11. A process according to claim 1, wherein the reducing agent is molecular hydrogen or formic, acetic or propionic acid.

* * * * *